(12) United States Patent
Sayre et al.

(10) Patent No.: US 8,236,936 B2
(45) Date of Patent: Aug. 7, 2012

(54) PRODUCTION OF RECOMBINANT SELENOPROTEIN MUTANTS WITH ENHANCED CATALYTIC ACTIVITY

(75) Inventors: Richard Sayre, Worthington, OH (US); Hangsik Moon, Morrisville, NC (US)

(73) Assignee: Ohio State University, Columbus, OH (US)

( * ) Notice: Subject to any disclaimer, the term of this patent is extended or adjusted under 35 U.S.C. 154(b) by 0 days.

(21) Appl. No.: 11/922,707

(22) PCT Filed: Jun. 21, 2006

(86) PCT No.: PCT/US2006/024093
§ 371 (c)(1),
(2), (4) Date: Mar. 11, 2010

(87) PCT Pub. No.: WO2007/002163
PCT Pub. Date: Jan. 4, 2007

(65) Prior Publication Data
US 2010/0159511 A1    Jun. 24, 2010

(51) Int. Cl.
*C07K 14/00* (2006.01)
*C07H 21/04* (2006.01)

(52) U.S. Cl. .................................... 536/23.1; 530/370
(58) Field of Classification Search ........................ None
See application file for complete search history.

(56) References Cited

OTHER PUBLICATIONS

Rubinelli et al., "Cadmium- and iron-stress-inducible gene expression in the green alga *Chlamydomonas reinhardtii* : evidence for H43 protein function in iron assimilation", Planta, 2002, 215:1-13.*
Fu et al., "A Selenoprotein in The Plant Kingdom: Mass Spectrometry Confirms That an Opal Codon (Uga) Encodes Selenocysteine in *Chlamydomonas reinhardtii* Glutathione Peroxidase", Journal of Biological Chemistry, 2002, 277(29):25983-25991.*
Tujebajeva et al., "Selenoprotein P Expression, Purification, and Immunochemical Characterization", Journal of Biological Chemistry, 2000, 275(9):6288-6294.*

* cited by examiner

*Primary Examiner* — Suzanne M Noakes
(74) *Attorney, Agent, or Firm* — Global Patent Group, LLC

(57) ABSTRACT

The present invention generally relates to the production of industrially relevant quantities of selenoprotein enzymes in eukaryotic cell cultures. More specifically, the present invention generally relates to the production of such enzymes wherein one or more catalytic cysteine or serine residues are mutagenically replaced by selenocysteine.

8 Claims, 4 Drawing Sheets

US 8,236,936 B2

PRODUCTION OF RECOMBINANT SELENOPROTEIN MUTANTS WITH ENHANCED CATALYTIC ACTIVITY

SEQUENCE LISTING

This application includes a sequence listing and is accompanied by a computer readable copy. The sequence listing appended to this application is identical to the computer readable copy.

BACKGROUND OF THE INVENTION

The present invention is generally directed to a method for producing industrially relevant quantities of catalytically enhanced recombinant enzymes. More particularly, the present invention is generally directed to such a process wherein the gene encoding the enzyme is a mutant that enables a catalytic cysteine or serine to be substituted with the selenium analog, i.e. selenocysteine.

Industrially relevant production of selenoproteins in non-animal or single celled systems has proven challenging because eukaryotic and bacterial selenocysteine insertion sequences (SECIS) operate differently. Bacterial SECISs are usually located immediately downstream of the UGA codon encoding selenocysteine. Thus, bacterial SECISs are translated. In contrast, typical eukaryotic SECISs are part of the 3' untranslated region (UTR) of the mRNA. The upshot of this architectural difference between bacterial and eukaryotic SECISs is that in order to express a eukaryotic gene in a bacterial cell you must add codons to the gene, which results in adding amino acids to the gene product. Accordingly, expressing a eukaryotic gene in bacteria is certain to affect the structure and likely to deleteriously affect the function of the recombinant protein.

Previously, others have demonstrated that *Chlamydomonas* has a eukaryotic SECIS. This suggested that it is possible to produce selenocysteine proteins in *Chlamydomonas*. However, the prior work was silent as to the catalytic benefit conferred by artificially replacing wild-type cysteine with selenocysteine and methods for secreting recombinant selenocysteine-containing proteins from *Chlamydomonas* under the control of a tightly regulated gene promoter.

The present invention provides methods for replacing cysteine and/or serine with selenocysteine. More particularly, the present invention provides a method of producing recombinant selenocysteine-containing proteins using any gene source, prokaryotic or eukaryotic, wherein the protein is catalytically enhanced through replacing cysteine and/or serine with selenocysteine. Accordingly, the present invention is novel and nonobvious, and thus deserves broad patent protection.

SUMMARY OF THE INVENTION

The present invention generally relates to a method for producing industrially relevant quantities of recombinant selenoproteins. More specifically, the present invention relates to a method for producing recombinant selenoprotein enzymes in which catalytically active cysteine or serine residue(s) are replaced by selenocysteine residues thereby yielding enzymes with enhanced catalytic activities. The present invention further relates to nucleic acids and cells transformed thereby that are instrumental in the method of the present invention. The present invention also relates to a cassette that reduces expression of other periplasmic-targeted proteins to facilitate purification of the secreted selenoproteins.

DETAILED DESCRIPTION OF THE INVENTION

Figure 1:
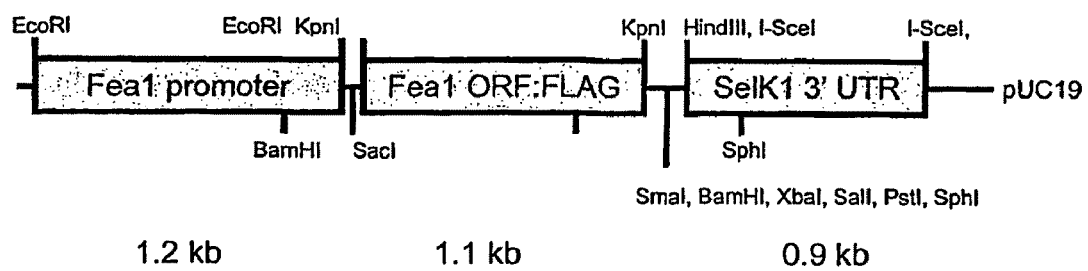
FIG. 1 is a diagram of the recombinant selenocysteine expression vector, pMOON3.

The present invention is generally directed to a method for producing industrially relevant quantities of recombinant selenoprotein enzymes. More particularly, the present invention generally relates to a method for producing recombinant enzymes having enhanced catalytic activity due to the substitution of at least one cysteine (Cys) or serine (Ser) residue with at least one selenocysteine (Sec). The present invention further relates to nucleic acids and cells transformed thereby that are instrumental in the method of the present invention. The present invention also relates to a cassette that down-regulates expression of other periplasmic-targeted proteins to facilitate purification of the recombinant selenoproteins.

The process of the present invention generally comprises the following steps. A host is selected based upon its capacity for producing selenoprotein in cell culture. An expression vector, such as a plasmid, is provided for encoding the desired gene product. The host cell is then transformed by the expression vector through any of a variety of known methods including transfection, electroporation, the glass bead method, and the like. Next the cells are subjected to a selection process, which tends to kill non-transformed cells while permitting transformed cells to reproduce. Then the selected cells are cultured in a medium permitting expression of the gene product. Finally, the gene product is isolated by any of a variety of suitable processes.

In general, any of a variety of suitable host cells may be used for producing recombinant selenoproteins. A key feature of a suitable host includes the capacity to biosynthetically produce one or more selenoproteins using an untranslated insertion sequence. Both animal and eukaryotic algal cells are generally capable of producing selenoproteins in this way. Accordingly, an embodiment of the present invention comprises using animals or animal cell cultures to produce recombinant selenoproteins. More preferably, an embodiment of the present invention comprises using a eukaryotic algal cell culture to produce recombinant selenoproteins. Still more preferably an embodiment of the present invention comprises using *Chlamydomonas reinhardtii* cell culture to produce recombinant selenoproteins.

Any of a variety of suitable expression cassettes can comprise an embodiment of the present invention. A suitable expression cassette typically contains a promoter sequence, a gene product encoding sequence, and an optional selection sequence; although, selection sequences may be introduced separate from the expression vector by co-transformation using an additional plasmid. Furthermore, a suitable expression cassette may optionally contain a signal sequence. Additionally, a suitable expression cassette may optionally contain a sequence coding for an RNAi that down-regulates expression of interfering genes. Expression cassettes are generally contained within expression vectors.

The function of the control sequence is to switch expression on and off. The promoter's switching function is ideally absolutely on or absolutely off; however, in practice such promoters are very unusual. Thus, a preferable promoter remains in predominantly two states; namely, substantially on, or substantially off. More preferably such a promoter is additionally characterized by the capacity to induce a high degree of transcription inasmuch as this increases downstream protein synthesis. Thus, in one embodiment the control sequence comprises the Fea1 promoter sequence (SEQ ID 1).

The expression cassette's gene product encoding sequence can encode any of a wide range of selenoprotein genes. Moreover, substantially similar expression cassettes may be used to biosynthesize any of a variety of selenoproteins by changing only the gene product encoding sequence. Thus, the process of the present invention may be used to produce a wide range of recombinant selenoproteins with relatively little effort.

As noted above, the expression cassette may optionally contain a selection sequence and/or a signal sequence. Selection sequences are discussed in more detail below; however, in general terms a selection sequence enables one to purge non-transformed cells from a cell culture thus leaving substantially only transformed cells. Signal sequences include translated portions of a gene that cause the gene product to include a proteinaceous targeting sequence so that it tends to accumulate in a particular region.

Additionally, as noted above, the expression cassette may optionally contain a sequence coding for an RNAi that down-regulates expression of an interfering gene product. For instance, when the Fea1 gene promoter is used in combination with a recombinant gene product sequence the wild-type Fea1 protein may interfere with and/or contaminate the recombinant gene product. Thus, in such instances it is desirable to down-regulate expression of the wild-type Fea1 gene product. Down-regulation can be accomplished by including a copy of at least a portion of the translated wild-type gene in reverse orientation thus forming a fold-back structure that can be processed by the dicer complex yielding small interfering RNA or RNAi fragments. These fragments bind to the translated region of the wild-type gene in an antisense orientation thereby down-regulating expression.

Figure 4:
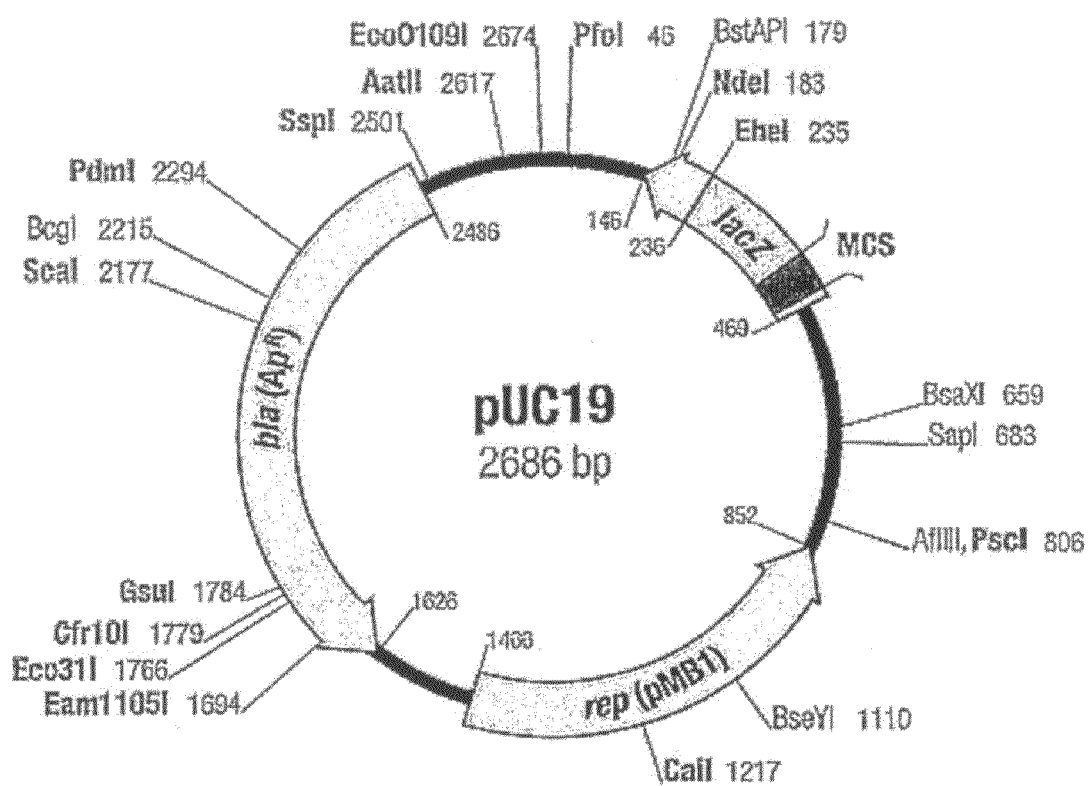
FIG. 4 is a diagram of the pUC19 plasmid.

In practice, the expression cassette is typically incorporated into an expression vector such as a plasmid. Any of a variety of plasmids may be used in connection with the process of the present invention. Characteristics of a suitable plasmid include the ability to transform a cell. More particularly, such characteristics include the capacity to induce one or more cells to produce a gene product encoded on the plasmid. Preferably, such a plasmid has the capacity to produce a gene product by a process that can be controlled, for instance, by altering conditions such as chemical content of the growth media. Plasmids within the scope of the present invention include without limitation the pUC18 plasmid, and the pUC19 plasmid as shown in FIG. 4.

A plasmid containing an expression cassette can be introduced to a host cell in any one of a variety of suitable ways, thereby transforming the cell. For instance, in one embodiment the host cells are transfected by a virus containing the plasmid. Alternatively, the plasmid can be introduced to the host cell through electroporation. A still further embodiment comprises introducing the plasmid to the host cell through the glass bead method. One of skill in the art will recognize that other methods for accomplishing transformation are also suitable, and are thus encompassed by the present invention. Any combination of the foregoing transformation methods are also within the scope of the present invention.

Following transformation, the cells are generally subjected to a selection process. A wide variety of known selection methods are consistent with the present invention. For example, an embodiment of the present invention comprises transforming at least one cell with a gene that confers antibiotic resistance. Thus, transformed cells can be selected by subjecting the entire population to antibiotics. Alternatively, an embodiment comprises transforming a host cell with a gene that confers it with the ability to biosynthesize one or more amino acids, such as arginine, which it would otherwise be unable to produce on its own. Thus, transformed cells can be selected by growing the cells on media deficient in that amino acid. One of skill in the art appreciates that a large number of alternative selection processes are known that are consistent with, and are thus encompassed by, the present invention. Any one of the foregoing selection methods explicitly enumerated or implicitly encompassed by the present invention, or any combination thereof, can comprise an embodiment of the present invention.

After the cells have been subjected to a selection process they are cultured in or on a medium that promotes expression of the desired gene product. Any of a wide variety of known culturing methods can comprise an embodiment of the present invention. In general, suitable culture methods are characterized by inducing the promoter gene to begin producing the desired gene product. For instance, the media can contain one or more chemical species at a sufficient level to induce translation. Conversely, the media can be deficient in one or more chemical species such that translation is induced. Suitable media include without limitation liquid broths and gelatinous media. Specific growth conditions and nutrients are limited only by the requirements of the selected host cell.

If an optional signal sequence is used then the gene product may accumulate any of a variety of convenient locations. For instance, a signal sequence could cause the gene product to be secreted from the host cell. One non-limiting example of a signal sequence is that of the Fea1 gene. The Fea1 gene codes for an iron assimilating protein known as the Fea1 protein, and the Fea1 signal sequence codes for a gene product that causes the Fea1 protein to accumulate between the cell membrane and wall. Thus, host cells lacking a cell wall secrete the enzyme rather than accumulate it. It is appreciated by those skilled in the art that there are numerous alternative methods for targeting gene products. Thus, the foregoing non-limiting example is merely illustrative, and does not exclude such alternative embodiments.

Finally, the gene product is collected or isolated by any of a wide variety of suitable known methods. For instance, the gene product may be precipitated, extracted, filtered, centrifuged, or any combination thereof. More specifically, if the gene product is secreted then the cells can be separated from the media by centrifugation, and the gene product can be salted out of the media and collected by filtration. Alternatively, the cells can be lysed and then separated by centrifugation followed by salting the gene product out of the media. A still further example comprises either of the foregoing methods in combination with any of a variety of suitable forms of liquid chromatography including size exclusion chromatography, HPLC, reverse phase HPLC, and the like.

The method of the present invention encompasses a wide variety of catalytically active proteins. More specifically, the scope of the present invention encompasses any protein enzyme having a Cys or Ser in its active site because such enzymes can benefit by replacing the catalytic Cys or Ser with selenocysteine. More specifically, the sulfhydryl of Cys and the hydroxyl of Ser are much weaker nucleophiles than the selenium hydride of selenocysteine, which imparts less biologically favorable ionization and reducing potentials in comparison to selenocysteine. Thus, replacing catalytic Cys and/or Ser with selenocysteine can result in recombinant selenoproteins with higher catalytic turnover numbers and improved physiological activity profiles in comparison to the natural enzyme. Accordingly, examples of enzymes encompassed by the process of the present invention include without limitation hydrogenase, glycine reductase, selenoprotein B, proline reductase, formate dehydrogenase, glutathione peroxidase, thioredoxin reductase, selenoproteins W and P, and phospholipid hydroperoxide glutathione peroxidase, urease, fatty acid elongase, papain, Fea1 and the like.

EXAMPLE 1

In one embodiment of the present invention the recombinant gene product comprises a selenocysteine analog of the Fea1 protein. As shown in FIG. 1, the expression cassette of this embodiment includes a Fea1 promoter at the 3' end (see SEQ ID 1), a gene encoding either a wild-type or seleno-analog of Fea1 (see SEQ ID 2). The Fea1 gene includes a 5' periplasmic targeting sequence. An optional immuno-tagging sequence known as the FLAG epitope is located just downstream from the signal sequence (see SEQ ID 4 and 5). Finally, an untranslated Sec insertion sequence, which is part of the SelK1 terminator sequence, is located at the 3' end of the expression vector (see SEQ ID 3). The gene encoding Fea1 may be either wild-type (Fea1-FWT) or the selenocysteine analog (Fea1-Sec188). Each of the foregoing sequence are incorporated into multicloning site of the pUC19 plasmid expression vector (See FIG. 4 and SEQ ID 6).

In the Fea1 embodiment the expression vector's promoter sequence is also the promoter of the Fea1 protein found in non-transformed *Chlamydomonas* cells. Therefore, in order to demonstrate that transformation was successful an optional tag sequence was included in a translated portion of the expression vector, thereby immuno-labeling the N-terminus of the mature recombinant gene product. Accordingly, the expression vector's product can be readily distinguished from that of non-transformed cells by western blot analysis, as shown in FIG. 3.

Figure 3:
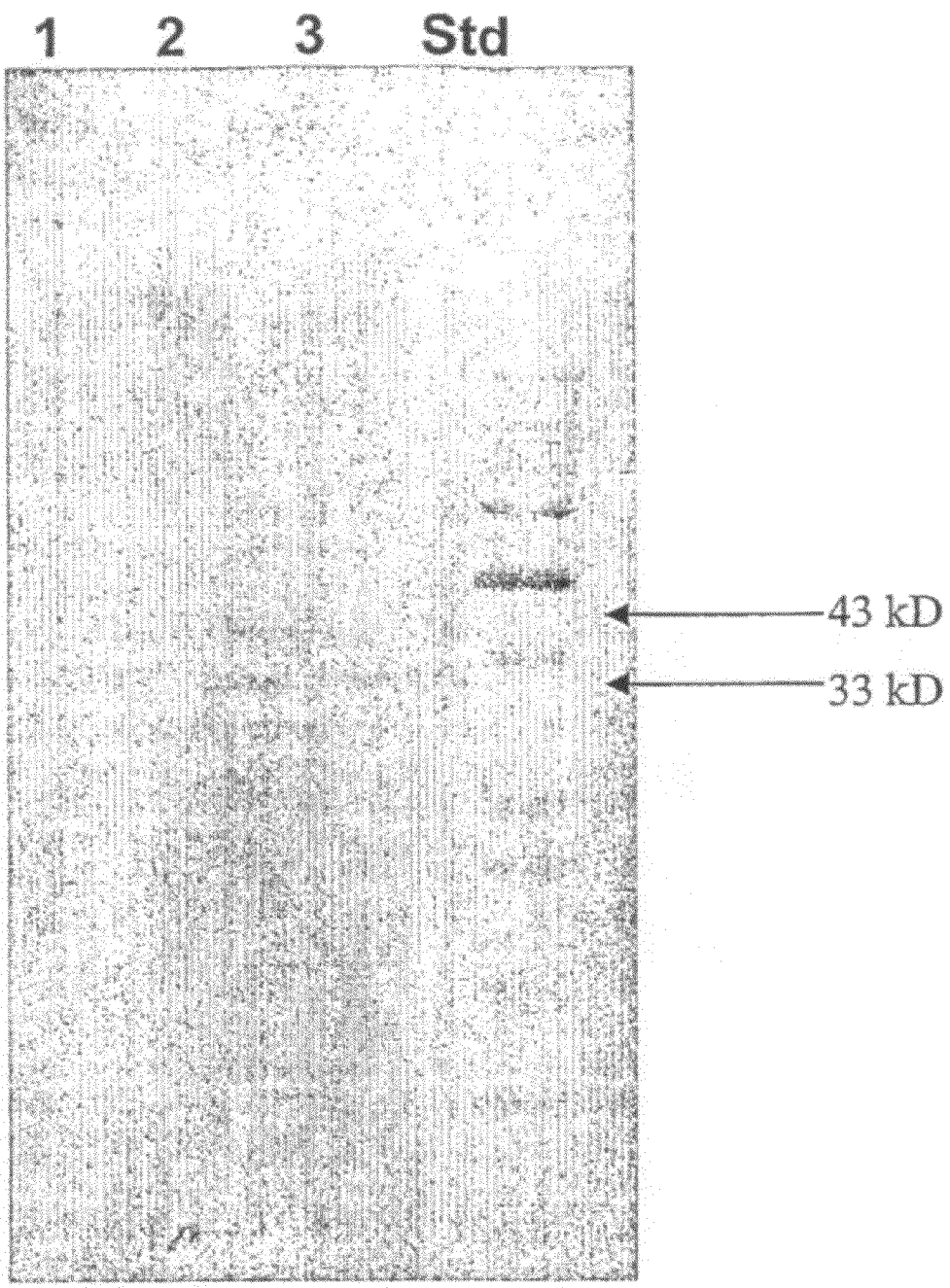
FIG. 3 is a western blot of supernatant proteins isolated from wild-type, untransformed cells (lane 1), Fea1-Sec188 (lane 2) and Fea1-FWT (lane 3) transgenic cells. Each lane contains 2.5 µg of total protein.

The Western blot of FIG. 3 contains four lanes. Lane 1 contains protein isolated from wild-type, untransformed cells. Lane 2 contains protein isolated from Fea1-Sec188 transgenic cells. And lane 3 contains protein isolated from Fea1-FWT transgenic cells. The lane labeled "std" contains a molecular weight standard. More particularly, lane 3 includes a FLAG-tagged version of the wild-type Fea1 gene (Fea1-FWT), and lane 2 includes a FLAG-tagged Fea1 gene in which a stop or Sec codon (UGA) is introduced at codon 188 (Cys, UGC). In this blot, the FLAG-epitope is introduced into both the Fea1-FWT as well as Fea1-Sec188 genes to distinguish the recombinant proteins from that of the non-transformed cells. Notably, the tag sequence is not required for production purposes, and is only used here to demonstrate successful transformation and expression of recombinant proteins. Thus, the tag is optional, rather than a necessary component of the present invention.

As shown in FIG. 1, the Fea1-FWT and Fea1-Sec188 genes are cloned into the selenocysteine expression vector, pMOON3. Thus the pMOON3 expression vector comprises either the wild-type gene or the selenocysteine mutant gene. The pMOON3 vector further includes a Fea1 promoter sequence that is inducible by elevated carbon dioxide, low iron, or high cadmium levels. The pMOON3 vector also includes a multicloning site, and a *Chlamydomonas* selenocysteine insertion sequence (SECIS) denoted SelK1 located in the 3' position.

Both the wild-type and selenocysteine mutant pMOON3-Fea1 vectors are used in combination with the p389 plasmid to simultaneously transform host cells. That is, cells are subjected to either a mixture of pMOON3-Fea1-FWT and p389, or pMOON3-Fea1-Sec188 and p389; however, transformed cells do not contain both the pMOON3-Fea1-FWT and pMOON3-Fea1-Sec188 expression vectors. The function of the p389 plasmid is to encode the ARG7 gene, which imparts the host cell with the capacity to produce its own arginine. Since the host cell is an arginine auxotroph, it is not capable of producing its own arginine in the absence of p389. Thus, transformed cells can be selected by growing the population on arginine deficient media.

The *Chlamydomonas* host, CC-424, is transformed by the glass bead method. Transformants containing the integrated pMOON3 expression vectors and p389 selection sequence are identified by PCR using primer sets to amplify across Fea1/SelK1 3' UTR junction. PCR-confirmed Fea1-FWT and Fea1-Sec188 transformants, as well as untransformed wild-type cells (CC-424), are inoculated into 25 mL of arginine deficient Tris-acetate-phosphate (TAP) medium. Thus, substantially only cells that are successfully transformed are able to survive. Following ten days of growth the cells are collected, washed twice with TAP iron-deficient medium containing 100 µg/L sodium selenite, and inoculated into 1 liter of TAP containing sodium selenite (100 µg/L) and low iron (0.5 µM Fe) thus inducing Fea1 gene expression. Most of the gene product is secreted in the first six hours following induction, i.e. subjection to low iron or high carbon dioxide conditions. After four days of growth, the cultures are adjusted to 0.1 M NaCl, 1 mM ε-amino-n-caproic acid, and agitated at 150 rpm for ten minutes before the cells are removed from the growth medium by centrifugation at 4,000 g and 4° C. for five minutes. The supernatants are filtered through 0.2 µm membrane to remove any remaining cells. Solid ammonium sulfate is added to 80% saturation and the solution is stirred for an hour at 4° C. to precipitate secreted proteins. The precipitated supernatant proteins are collected by centrifugation at 23,400 g and 4° C. for 90 minutes, resuspended in 5 mL of buffer A (50 mM Tris-HCl, 10 mM EDTA, 1 mM phenylmethylsulfonyl fluoride (PMSF), 1 mM ε-amino-n-caproic acid), and reprecipitated by adding 100% ice cold trichloroacetic acid (10% (w/v) final concentration) and allowing the precipitate to stand for one hour at 4° C. The precipitated proteins are collected by centrifugation at 20,000 g and 4° C. for 30 minutes, and resuspended in buffer B (0.1 M $Na_2CO_3$, 0.1 M dithiothreitol). Equal amounts of proteins are resolved on a 12% polyacrylamide gel and visualized by staining with Coomassie blue.

Figure 2:
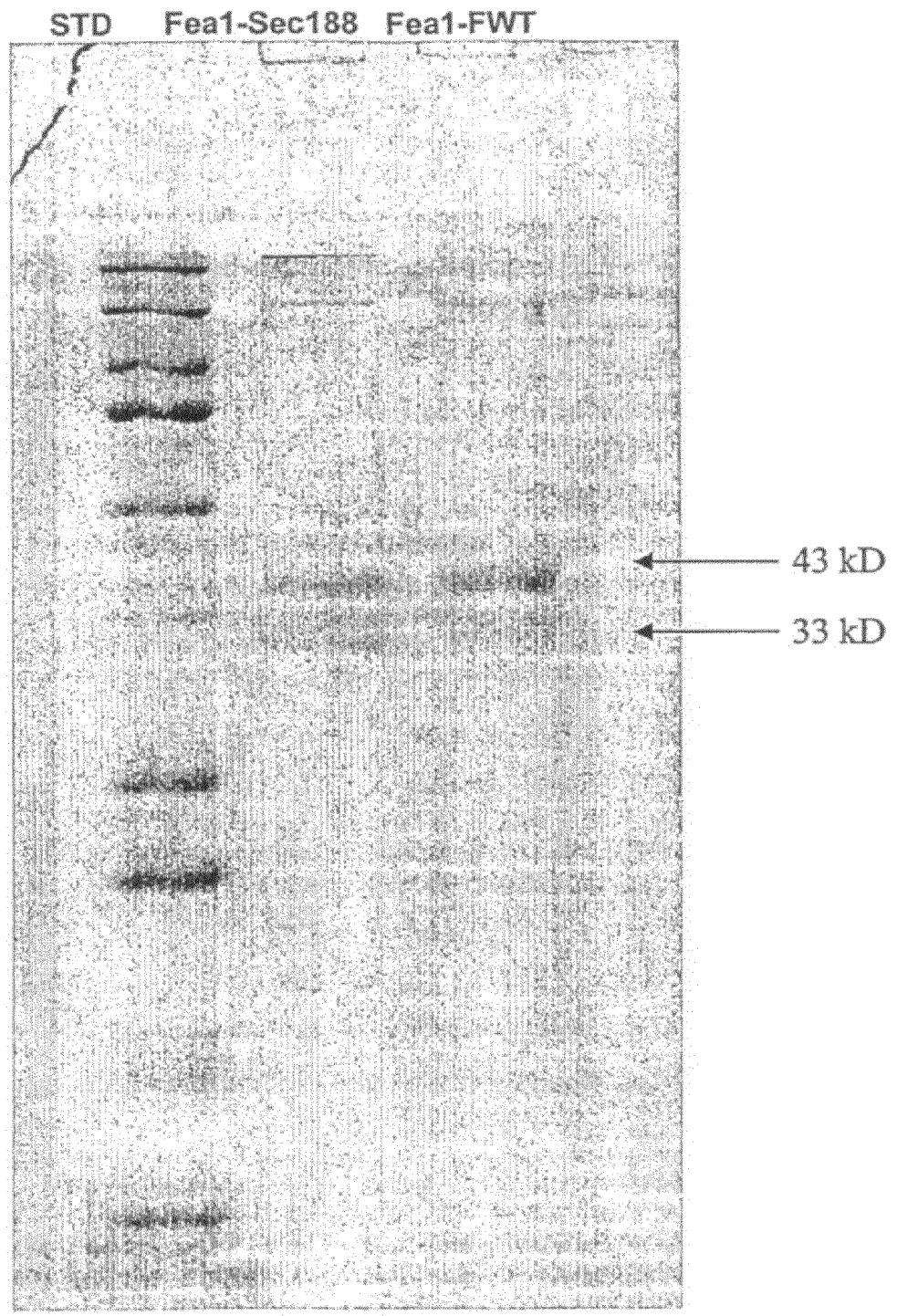
FIG. 2 is a coomasie blue stained gel of secreted proteins isolated from Fea1-FWT and Fea1-Sec 188 cells. Each lane has 20 µg protein loaded.

As shown below in FIG. 2, a doublet band is observed migrating at approximately 43 kD in both the Fea1-FWT and Fea1-Sec188 transgenic lanes. Previous results have demonstrated that the Fea1 protein runs as single bands at 43 kD (upper arrow) and at 33 kD (lower arrow) on SDS-PAGE. Significantly, there is no truncated Fea1 protein (188 versus 327 amino acid full length) present in the supernatant fractions obtained from Fea1-Sec188 cells. This indicates that a selenocysteine was successfully introduced at the mutant stop codon thus allowing full-length expression of the Fea1-Sec188 protein. Notably, due to limited Fea1 protein production from non-transgenic or WT cells no coomassie blue-stained proteins are visualized in FIG. 2 indicating that no such protein is isolated from the supernatant of untransformed or WT cells.

Since both recombinant Fea1 genes introduced into the pMOON3 expression vector include FLAG-epitopes recombinant Fea1 proteins can be distinguished from and that of the non-transformed cells by western blot analysis using an anti-FLAG antibody. As shown in FIG. 3 below, two co-migrating protein bands are detected by anti-FLAG antibody at 43 and 33 kD in the supernatant fraction obtained from the recombinant Fea1-FWT and Fea1-Sec188 cultures. A very weak non-specific band migrating between the 43 kD and 33 kD bands is detected in the supernatant fraction from untransformed cells.

Thus, both the 43 and 33 kD proteins detected in recombinant supernatant fractions (i.e. that of Fea1-Fwt and Fea1-Sec188) are full-length FLAG-tagged Fea1 proteins. The faster migrating form (33 kD) of the Flag-immuno-detected protein is likely either a non-glycosylated or a partially degraded form of the Fea1 protein.

Notably, the process of the present invention in accordance with the foregoing example produces 2 mg of Fea1-Sec188 protein per liter of culture. Such a yield suggests that it is feasible to produce recombinant selenoprotein mutants from algal cell cultures in commercially relevant quantities. And, unlike bacterial cell cultures, this includes post-translationally modified proteins.

EXAMPLE 2

Another embodiment of the present invention is similar to Example 1 except that the gene product encoding sequence codes for a mutant papain enzyme. More particularly, Cys-25 is replaced by Sec-25. Papain is a widely used industrial enzyme that is limited in its application in part due to its low specific activity relative to other proteases such as trypsin. However, replacement of the active site's Cys-25 with Sec-25 results in enhanced catalytic activity that increases papain's cost-competitiveness with trypsin.

According to the papain embodiment, a selenoprotein expression vector is provided for expressing recombinant selenoproteins in *Chlamydomonas*. The vector is a plasmid substantially similar to that of the Fea1 example above; however, the vector codes for papain rather than Fea1. More specifically, the plasmid comprises: 1) the highly inducible *Chlamydomonas* Fea1 promoter, 2) an optional Fea1 signal sequence causing secretion of the selenoprotein gene product into the media, 3) a sequence encoding the papain enzyme; and 4) a 3' Selk1 *Chlamydomonas* Sec-insertion sequence (SECIS) for inserting the tRNAsec into the ribosome at engineered Sec codon(s).

EXAMPLE 3

A still further example of the present invention is essentially identical to Example 2 except that the expression vector additionally includes a sequence encoding an RNAi for down-regulating wild-type Fea1 protein production.

EXAMPLE 4

Still another example of the present invention is essentially identical to Example 1 except that the gene product encoding sequence codes for a fatty acid elongase, and lacks a signal sequence. Thus the gene product is not secreted from the cell, but rather accumulates therein. More specifically, a plasmid consistent with this example comprises: 1) the highly inducible *Chlamydomonas* Fea1 promoter, 2) a sequence encoding the fatty acid elongase; and 3) a 3' Selk1 *Chlamydomonas* Sec-insertion sequence (SECIS) for inserting the tRNAsec into the ribosome at engineered Sec codon(s).

The foregoing examples are considered only illustrative of the principles of the invention rather than an exclusive list of embodiments. Further, since numerous modifications and changes will readily occur to those skilled in the art, the invention is not intended to be limited to the exact construction and operation shown and described, and accordingly, all suitable modifications and equivalents are within the scope of the present invention.

We claim:

1. A DNA nucleotide sequence of which consists of SEQ ID NO: 2.

2. An expression vector comprising the nucleic acid sequence of claim 1 operably linked to an expression control sequence.

3. A cultured cell comprising the nucleic acid sequence of claim 1 operably linked to an expression control sequence, wherein the cell is eukaryotic.

4. A cultured cell transformed with the expression vector of claim 2, or a progeny of said cell, wherein the cell expresses a selenoprotein, and wherein the cell is eukaryotic.

5. A process for producing selenoproteins comprising the steps of:
   culturing the cell of claim 3 under conditions permitting expression of a selenoprotein under the control of the expression control sequence; and
   isolating the selenoprotein from the cell or from the medium of the cell.

6. A selenoprotein made according to the process of claim 5.

7. A process for producing selenoproteins comprising the steps of:
   culturing the cell of claim 4 under conditions permitting expression of a selenoprotein under the control of the expression control sequence; and
   isolating the selenoprotein from the cell or from the medium of the cell.

8. A selenoprotein made according to the process of claim 7.

* * * * *

SEQUENCE LISTING

```
<160> NUMBER OF SEQ ID NOS: 6

<210> SEQ ID NO 1
<211> LENGTH: 1203
<212> TYPE: DNA
<213> ORGANISM: Artificial
<220> FEATURE:
<223> OTHER INFORMATION: vector

<400> SEQUENCE: 1
taccaggaca gagtgcgtgt ggccagggca caggcgccca tccagcagct cgccgtctaa      60
gtaggccgtc catgcagtgc cggtcgggtc cggaaccacg aaccagtggt gagggaaaac     120
atcgttacgc tctgggtgag cactacacga tgggtattcc tcaattagtt ccgggtaagc     180
gacaaccgag cgagtcgccg cgagtgcaag cagtgcaatt gacaggctga acgcggccat     240
cggcaatccg cagcggaact gtctcaattt acttcgtgac ctatgtatgt tgaatatgct     300
gtcgggtcga ccagcggcca gtaggagtgg ccactcggtg tggaagagtg ggccgcgctg     360
gactgctggc gcgacctttg aacgcggaca acttgcaaaa gtatttgatt atcatcaacg     420
caaaagtgat gctggcgaat tggagggggc gccgcgaggc acgcgccagg ctgctgcgcg     480
```

```
cttgccatgc gcgtgccggg tctgtccgag agtcgagcca agtcgctgct ttatgacaca    540
acaatatatc gttagttgct ctgaaggcga ccaagaacct cgcggggcgt gctaatgtag    600
gagaaacaag caagcaaccg acacgaacca gcttgctttc ccgccgtgca gttaatgcat    660
gtgcgcatgg atgcatgaaa ttcctatgga agctgcgcat ttcccacatt gaaaaacgag    720
cgcgaaaaac gcgcgtagga gtgcatcgtg cgtgcctttt aagcgatgtg tgcgtgcaaa    780
gtattgcatt ataattgcat gataactctt gtatgtttag agtcagtagg cagggccgg    840 ccggcagtca gacctggatt ggcgacacaa gtctgccagg acgactgcgg tggcaaagtt    900
ggtggagatt ttcgagttgg agctcctctg tgtctgtgtc agacactcta actttcttgt    960
ctcctgtttt ctgctttgcc tttcagcggc cggttgcatt ggatgtacaa gtgtggcgtg   1020
tggaaagcgc gcacgacacg cgcgcgcgac gcccgccgcg gctggcacca gcctggcgct   1080
ggatccaatc tgctgcacgc cgcgcataaa tgcaagtgtc tactgtgata ttggcataat   1140
ttaaacactc cccactggct cactaggact attgctgctc gcaagcccgt cgcacagtta   1200
acc                                                                 1203

<210> SEQ ID NO 2
<211> LENGTH: 1113
<212> TYPE: DNA
<213> ORGANISM: Artificial
<220> FEATURE:
<223> OTHER INFORMATION: vector

<400> SEQUENCE: 2
atgtcggtcg gatttctggt cctcgcgctg ggcgcgcttg tcgtggcgac ggcggactac     60
aaggacgacg acgacaagca gcccacgacg actggcactc gcttcgaggg ttttctcttac   120 gcgggcaatg tcattggcta tgtgaacatg acgatggact actgcgacat caaggccgcc   180
atggctgctg gcaacttcac cgaggctctg tccatctact ctactggcaa gaactcgttc   240
tctggcctgg cgcgccgcac cttcttccgc ttcgcctcgt acatcaccgc caacggctcc   300
gtggagccgc tgcacgactc catcctggcc ggcaaggaca cgtcctccct ggacgccgcc   360
atccgggctg ccctggccga cggcaaggcc accctggccg ccggtctgat ccaggtgggc   420
acgctcaagt accacctgca cgaggtggat gaggcctaca acaagatcaa gacctacctg   480
gctgacggca ccggcaacct caccaacctg gtttctgacg cctcgggcgc accccacaac   540
gtggatgagg cctgggcgct gtgggccggc ggcgccgcca acaactgagg caccctgtcc   600
ggctgggcct cctccctggg cgccgccatg gcaccacct tcctcggcaa gagctatgtc   660
aacaccgcca tgatcaacac cgtcaatgag atgctggccg ccgcccgcct gtctaccctg   720
aacatccaag cctacgacgc cgcgcgcacg aacgaggtcc gactgctgac cctgctgggc   780
ctgcagggcg tgtccgtggc cgcgtacacc gctgacgccg ccgccgcctg caagcgcccc   840
gccgccgagg tggaggatgc caagaccatg atcgccgtgc actgggcgta cctggagcct   900
atgctcaagc tgcgcaactt caaggcctcc gccgtgaccg agctgcacca ccagctcacc   960
gcctccaagc tgagctacaa gaaggtggcc gccgcggtga agggcgtgct gtcggctatg  1020
ggccgccgct ccagcgagct gggtgccccg cagtccgcca tcattgccgc caactggaag  1080
tgcagctcca agaccctgcg cagcattgcg taa                               1113

<210> SEQ ID NO 3
<211> LENGTH: 872
<212> TYPE: DNA
<213> ORGANISM: artificial
<220> FEATURE:
```

<223> OTHER INFORMATION: vector

<400> SEQUENCE: 3

```
agtgcgcctg ctgagcactg cttgcggagc ctctttcgtg aaaagcgcgt ccgtatggtt      60
agatagcagt gctctggagc aggtctggtg catggttgga tgatcgggta tgtgcatatc     120
atgcgggcaa cacactcgct ttctaggttg ctgatggagc caaccttgct gaagtgtagt     180
gtgtgcatgc agagagtgca cagcaggata gccttctggc ggaatgctgc gctgcttcat     240
cacatgtagt gcgtggtaac cgcgggatac ggcgtccagc cccgatttgt caagtttggt     300
cgtggcgttc tggcatacat tgtttgcact ctgtgaagcg ctttcggccc caaaggttca     360
tcacctaagg aactgcaagt gcatggatgc agaaggact gcgccaatgg ctttcgttta      420
tgacggtcct ggctagaatg cttggcttgg acccgagcta cagaaagctg cagcttgata     480
ttggactggt ggcaggtgca ggagggtaag gcttagacc acaaggtgtg tgagtagcag      540
atggagcgcg gactaatcta ggtgatttag ggcgcggtgg agggtgaggt ggttggcgct     600
tcggttctcg ggtctgactt tttgcaggtg gcatattcaa tagcacttgc aggtatgaga     660
gctagacggc ccgtatcagg catctgccgt gcggttgca atgtggagat gtacatgcag      720
gcagcaggca gcaagtagcg gagtcaaggc tgtgtgatac acgcagggta cgtgcaaggc     780
acggagcgt gctgccagag ggacctagca gatcaacaat tggaaccaaa ctggcaggtt      840
ttggtttgat tgtgcaagag tttgcgcgct gc                                   872
```

<210> SEQ ID NO 4
<211> LENGTH: 24
<212> TYPE: DNA
<213> ORGANISM: Artificial
<220> FEATURE:
<223> OTHER INFORMATION: Vector

<400> SEQUENCE: 4

```
gactacaagg acgacgacga caag                                             24
```

<210> SEQ ID NO 5
<211> LENGTH: 8
<212> TYPE: PRT
<213> ORGANISM: Artificial
<220> FEATURE:
<223> OTHER INFORMATION: epitope

<400> SEQUENCE: 5

Asp Tyr Lys Asp Asp Asp Asp Lys
1               5

<210> SEQ ID NO 6
<211> LENGTH: 2686
<212> TYPE: DNA
<213> ORGANISM: Artificial
<220> FEATURE:
<223> OTHER INFORMATION: Vector

<400> SEQUENCE: 6

```
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg      120
ttggcgggtg tcgggctgg cttaactatg cggcatcaga gcagattgta ctgagagtgc      180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
```

```
tttcccagtc acgacgttgt aaaacgacgg ccagtgaatt cgagctcggt acccggggat    420
cctctagagt cgacctgcag gcatgcaagc ttggcgtaat catggtcata gctgtttcct    480
gtgtgaaatt gttatccgct cacaattcca cacaacatac gagccggaag cataaagtgt    540
aaagcctggg gtgcctaatg agtgagctaa ctcacattaa ttgcgttgcg ctcactgccc    600
gctttccagt cgggaaacct gtcgtgccag ctgcattaat gaatcggcca acgcgcgggg    660
agaggcggtt tgcgtattgg gcgctcttcc gcttcctcgc tcactgactc gctgcgctcg    720
gtcgttcggc tgcggcgagc ggtatcagct cactcaaagg cggtaatacg gttatccaca    780
gaatcagggg ataacgcagg aaagaacatg tgagcaaaag gccagcaaaa ggccaggaac    840
cgtaaaaagg ccgcgttgct ggcgtttttc cataggctcc gcccccctga cgagcatcac    900
aaaaatcgac gctcaagtca gaggtggcga acccgacag gactataaag ataccaggcg    960
tttccccctg gaagctccct cgtgcgctct cctgttccga ccctgccgct taccggatac    1020
ctgtccgcct ttctcccttc gggaagcgtg gcgctttctc atagctcacg ctgtaggtat    1080
ctcagttcgg tgtaggtcgt tcgctccaag ctgggctgtg tgcacgaacc ccccgttcag    1140
cccgaccgct gcgccttatc cggtaactat cgtcttgagt ccaacccggt aagacacgac    1200
ttatcgccac tggcagcagc cactggtaac aggattagca gagcgaggta tgtaggcggt    1260
gctacagagt tcttgaagtg gtggcctaac tacggctaca ctagaaggac agtatttggt    1320
atctgcgctc tgctgaagcc agttaccttc ggaaaaagag ttggtagctc ttgatccggc    1380
aaacaaacca ccgctggtag cggtggtttt tttgtttgca agcagcagat tacgcgcaga    1440
aaaaaaggat ctcaagaaga tcctttgatc ttttctacgg ggtctgacgc tcagtggaac    1500
gaaaactcac gttaagggat tttggtcatg agattatcaa aaaggatctt cacctagatc    1560
cttttaaatt aaaaatgaag ttttaaatca atctaaagta tatatgagta aacttggtct    1620
gacagttacc aatgcttaat cagtgaggca cctatctcag cgatctgtct atttcgttca    1680
tccatagttg cctgactccc cgtcgtgtag ataactacga tacgggaggg cttaccatct    1740
ggccccagtg ctgcaatgat accgcgagac ccacgctcac cggctccaga tttatcagca    1800
ataaaccagc cagccggaag ggccgagcgc agaagtggtc ctgcaacttt atccgcctcc    1860
atccagtcta ttaattgttg ccgggaagct agagtaagta gttcgccagt taatagtttg    1920
cgcaacgttg ttgccattgc tacaggcatc gtggtgtcac gctcgtcgtt tggtatggct    1980
tcattcagct ccggttccca acgatcaagg cgagttacat gatcccccat gttgtgcaaa    2040
aaagcggtta gctccttcgg tcctccgatc gttgtcagaa gtaagttggc cgcagtgtta    2100
tcactcatgg ttatggcagc actgcataat tctcttactg tcatgccatc cgtaagatgc    2160
ttttctgtga ctggtgagta ctcaaccaag tcattctgag aatagtgtat gcggcgaccg    2220
agttgctctt gcccggcgtc aatacgggat aataccgcgc cacatagcag aactttaaaa    2280
gtgctcatca ttggaaaacg ttcttcgggg cgaaaactct caaggatctt accgctgttg    2340
agatccagtt cgatgtaacc cactcgtgca cccaactgat cttcagcatc ttttactttc    2400
accagcgttt ctgggtgagc aaaaacagga aggcaaaatg ccgcaaaaaa gggaataagg    2460
gcgacacgga aatgttgaat actcatactc ttcctttttc aatattattg aagcatttat    2520
cagggttatt gtctcatgag cggatacata tttgaatgta tttagaaaaa taaacaaata    2580
ggggttccgc gcacatttcc ccgaaaagtg ccacctgacg tctaagaaac cattattatc    2640
atgacattaa cctataaaaa taggcgtatc acgaggccct ttcgtc                   2686
```